United States Patent
Kolbe et al.

(10) Patent No.: US 10,245,252 B2
(45) Date of Patent: Apr. 2, 2019

(54) USE OF ALKYLAMIDOTHIAZOLES IN COSMETIC OR DERMATOLOGICAL PREPARATIONS FOR THE PROPHYLAXIS OR TREATMENT OF SENSITIVE SKIN

(71) Applicant: BEIERSDORF AG, Hamburg (DE)

(72) Inventors: Ludger Kolbe, Dohren (DE); Cathrin Scherner, Norderstedt (DE); Ursula Wennsorra, Hamburg (DE); Tobias Mann, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 15/104,463

(22) PCT Filed: Nov. 21, 2014

(86) PCT No.: PCT/EP2014/075319
§ 371 (c)(1),
(2) Date: Jun. 14, 2016

(87) PCT Pub. No.: WO2015/090851
PCT Pub. Date: Jun. 25, 2015

(65) Prior Publication Data
US 2016/0324832 A1    Nov. 10, 2016

(30) Foreign Application Priority Data
Dec. 19, 2013 (DE) .......... 10 2013 226 711

(51) Int. Cl.
| | |
|---|---|
| A61K 31/426 | (2006.01) |
| A61K 8/49 | (2006.01) |
| A61Q 19/00 | (2006.01) |
| A61K 9/00 | (2006.01) |
| A61K 9/107 | (2006.01) |
| A61K 8/06 | (2006.01) |

(52) U.S. Cl.
CPC .......... *A61K 31/426* (2013.01); *A61K 8/062* (2013.01); *A61K 8/49* (2013.01); *A61K 9/0014* (2013.01); *A61K 9/107* (2013.01); *A61Q 19/005* (2013.01); *A61Q 19/007* (2013.01)

(58) Field of Classification Search
CPC ............... A61K 31/426; A61K 8/062
USPC .......................................... 514/371
See application file for complete search history.

(56) References Cited

U.S. PATENT DOCUMENTS

| | | | |
|---|---|---|---|
| 4,217,355 | A | 8/1980 | Harbert et al. |
| 8,920,785 | B2 | 12/2014 | Kolbe et al. |
| 2009/0247560 | A1 | 10/2009 | Ando et al. |
| 2013/0039870 | A1 | 2/2013 | Kolbe et al. |
| 2014/0121250 | A1 | 5/2014 | Kolbe et al. |
| 2016/0015613 | A1 | 1/2016 | Mann et al. |
| 2016/0015614 | A1 | 1/2016 | Mann et al. |
| 2016/0015615 | A1 | 1/2016 | Mann et al. |

FOREIGN PATENT DOCUMENTS

| | | |
|---|---|---|
| EP | 2072519 A1 | 6/2009 |
| WO | 2011117034 A2 | 9/2011 |
| WO | 2013041526 A1 | 3/2013 |
| WO | 2013041535 A1 | 3/2013 |
| WO | 2014139757 | 9/2014 |
| WO | 2014139758 A1 | 9/2014 |
| WO | 2014139759 | 9/2014 |

OTHER PUBLICATIONS

Brownskin.net [Internet] Retrieved on Feb. 20, 2017 [Retrieved from the internet] <url: http://www.brownskin.net/hyperpigmentation.html>.*
Drugs.com [Internet] Retrieved on Feb. 20, 2017 [Retrieved from the internet] <url: https://www.drugs.com/health-guide/eczema.html>.*
WebMd [Internet] Retrieved on Feb. 20, 2017 {Retrieved from the internet] <url: http://www.webmd.com/beauty/sensitive-skin-20-questions#1>.*

* cited by examiner

*Primary Examiner* — Brandon J Fetterolf
*Assistant Examiner* — Taina D Matos Negron
(74) *Attorney, Agent, or Firm* — Abel Law Group, LLP

(57) ABSTRACT

Use of alkylamidothiazoles in cosmetic or dermatological preparations for the prophylaxis and treatment of sensitive skin, itching, dry skin, and of inflammatory states of the human skin.

20 Claims, 3 Drawing Sheets

Fig. 1

USE OF ALKYLAMIDOTHIAZOLES IN COSMETIC OR DERMATOLOGICAL PREPARATIONS FOR THE PROPHYLAXIS OR TREATMENT OF SENSITIVE SKIN

BACKGROUND OF THE INVENTION

1. Field of the Invention

The present invention relates to the use of alkylamidothiazoles in cosmetic or dermatological preparations for the prophylaxis and treatment of sensitive skin, itching, and of inflammatory states in the human skin.

2. Discussion of Background Information

Changes associated with the aging process and extrinsic factors (e.g. damage to the skin barrier, effect of UV light, irritant or allergy-triggering substances, mechanical action e.g. due to shaving) can lead to skin irritation. In connection with this application, skin irritation is understood as meaning any change in the skin which triggers sensory discomfort in people or animals and/or is characterized by a dry, reddened and/or inflamed complexion. In this connection, the term "sensory discomfort" of course also encompasses conditions such as itching or pain. Skin irritation can encompass in particular phenomenologically different skin states: sensitive skin, including sensitive scalp, injured skin, dry skin, atopic and psoriatic skin, irritated skin, rosacea, inflamed skin, and also skin changes in diabetes mellitus, which manifests itself in the respectively higher degree of severity in skin reddening, so-called erythema.

The problem of "sensitive skin" is affecting a growing number of adults and children. It is in the meantime assumed that up to 50% of the population has sensitive skin (L. Misery et al., Ann. Dermatol. Venereol. 2005, 132, 425-429). Sensitive skin is the term used to refer to skin with a reduced irritancy threshold for irritants, such as hyperreactive and intolerant, but also atopic skin. In people with sensitive or injured skin, a phenomenon referred to as "stinging" ("to sting"=injure, burn, to cause pain) can be observed. Typically troublesome phenomena associated with the terms "stinging" or "sensitive skin" are skin reddening, tingling, prickling, tautening and burning of the skin and irritation. They can be brought about by stimulatory environmental conditions such as e.g. massage, action of surfactants, effect of other chemical substances such as e.g. lactic acid, weather influence such as heat, cold, dryness, but also wet heat, thermal radiation and UV radiation, e.g. the sun, or psychological stress.

"Sensitive" scalp is likewise characterized by skin reddening, tingling, prickling, burning and itching. Triggers are, for example, soap, shampoos or other haircare products, surfactants, hard water with high lime concentrations and/or mechanical stress. Erythema and hyperseborrhea (excess production of sebum) of the scalp as well as dandruff are often associated with the described phenomena.

In approx. 10-20% of the population of industrialized countries, atopy is observed with increasing tendency, a familiarly arising oversensitivity of the skin and mucosa to environmental substances, with increased readiness to develop oversensitivity reactions of the immediate type (allergies) to substances from the natural environment. Atopy is presumably determined by genetics. Atopy can manifest itself as atopic dermatitis. In this, the skin barrier is damaged, the skin is often inflamed and itches.

The erythematous effect of the ultraviolet part of solar radiation or synthetic radiation on the skin is generally known. Whereas rays with a wavelength which is less than 290 nm (the so-called UVC region) are absorbed by the ozone layer in the earth's atmosphere, rays in the range between 290 nm and 320 nm, the so-called UVB region, bring about an erythema, simple sunburn or even burns of greater or lesser severity. Erythematous skin symptoms also arise as accompanying symptoms in certain skin diseases or irregularities, for example acne, bacterially induced inflammations of the skin, cutaneous reactions, dermographism, soreness of the skin in general, sandworm disease, erysipelas, shingles, frostbite or burns. A particular form of skin reddening here is rosacea. Antiinflammatory preparations can therefore be used advantageously to combat skin redness due to general illness and specifically rosacea, to suppress them for a prolonged period and to largely prevent them from recurring.

Skin inflammation associated with reddening and itching is likewise brought about by insect bites. Antiinflammatory products can therefore also contribute to alleviating the consequences of an insect bite, such as e.g. reddening, wheal formation, itching and painful swellings of the skin, to suppress them for a prolonged period and to prevent them from recurring.

Erythema also occur to an increased extent in the nappy area of toddlers, and all the more so in babies (diaper dermatitis). Incontinence, a condition that occurs to an increased extent particularly in advancing years, is also often associated with erythema and skin reddening as a result of constant exposure to moisture and irritants (incontinence dermatitis).

Although a large number of active ingredients with skin-irritation-reducing effect are already used in the discussed technical areas, alternatives also continue to be sought.

In the cosmetic and pharmaceutical industry, there is therefore a constant need for products with a skin-irritation-reducing effect. In the search for corresponding anti-inflammatory products, it is to be ensured that the substances used in cosmetic and/or pharmaceutical products must also be
- toxicologically safe,
- highly skin compatible,
- stable (in particular in customary cosmetic and/or pharmaceutical formulations),
- preferably low-odor or (largely) odorless,
- preferably colorless or non-staining, and
- able to be manufactured in a cost-effective manner (i.e. using standard processes and/or starting from standard precursors).

The search for suitable (active) substances which have one or more of the specified properties to an adequate extent is made more difficult for the person skilled in the art by virtue of the fact that there is no clear dependency between the chemical structure of a substance on the one hand and its anti-inflammatory activity and its stability on the other hand. Furthermore, there is no predictable connection between the anti-inflammatory effect, the toxicological safety, the skin compatibility and/or the stability.

SUMMARY OF THE INVENTION

It was therefore the object of the present invention to indicate an anti-inflammatory active ingredient which preferably satisfies one or more of the aforementioned secondary conditions and particularly preferably all of the aforementioned conditions.

Surprisingly, it has been found that the use of alkylamidothiazoles in cosmetic or dermatological preparations for the prophylaxis and treatment of sensitive skin, itching, and inflammatory states in the human skin overcomes the disadvantages of the prior art.

Preferably, cosmetic or dermatological preparations according to the invention comprise 0.000001 to 10% by weight, particularly preferably 0.0001 to 3% by weight, and particularly preferably 0.001 to 1% by weight, of alkylamidothiazoles, based on the total weight of the preparations.

When using the active ingredients used according to the invention and/or cosmetic or topical dermatological preparations with an effective content of active ingredients used according to the invention, an effective treatment of, but also a prophylaxis in the case of deficient, sensitive or hypoactive skin states or deficient, sensitive or hypoactive states of skin appendages and/or inflammatory states and/or itching is surprisingly possible.

According to the invention, it is in particular extremely advantageous to use the active ingredient used according to the invention and/or cosmetic or topical dermatological preparations with an effective content of active ingredient used according to the invention for the cosmetic or dermatological treatment or prophylaxis of undesired skin conditions.

Advantageous alkylamidothiazoles in the context of the present invention are substances of the general formula in which
$R^1$, $R^2$, X and Y can be different, partly identical or completely identical and can mean, independently of one another:
$R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$-alkylamine (linear and branched), —$C_1$-$C_{24}$-alkylaryl (linear and branched), —$C_1$-$C_{24}$-alkylaryl-alkylhydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alky-morpholino, —$C_1$-$C_{24}$ alky-piperidino, —$C_1$-$C_{24}$ alky-piperazino, —$C_1$-$C_{24}$ alky-piperazino-N-alkyl,
$R_2$=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-hydroxyalkyl (linear and branched), —$C_1$-$C_{24}$-alkylaryl (linear and branched), —$C_1$-$C_{24}$-alkylheteroaryl (linear and branched),
X=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl (optionally mono- or polysubstituted with —OH, —F, —Cl, —Br, —I, —OMe, —NH$_2$, —CN), —$C_1$-$C_{24}$-heteroaryl (optionally mono- or polysubstituted with —OH, —F, —Cl, —Br, —I, —OMe, —NH$_2$, —CN), —$C_1$-$C_{24}$-alkylaryl (linear and branched), —$C_1$-$C_{24}$-alkylheteroaryl (linear and branched), -aryl (optionally mono- or polysubstituted with —OH, —F, —Cl, —Br, —I, —OMe, —NH$_2$, —CN), -phenyl, -2,4-dihydroxyphenyl, -2,3-dihydroxyphenyl, -2,4-dimethoxyphenyl, -2,3-dimethoxyphenyl,
Y=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cycloalkyl, —COO-aryl, —COO-heteroaryl,
and X, Y can optionally also=condensed aromatic,
where X and Y, among one another, can form aromatic or aliphatic homo- or heterocyclic ring systems with up to n ring-forming atoms, and where the number can assume n values from 5 to 8, and the respective ring systems can in turn be substituted with up to n−1 alkyl groups, hydroxyl groups, carboxyl groups, amino groups, nitrile functions, sulfur-containing substituents, ester groups and/or ether groups.

The specified thiazoles can be present either as free base or else as salt: e.g. as fluoride, chloride, bromide, iodide, sulfate, carbonate, ascorbate, acetate or phosphate. In particular as halogen salts, such as e.g. chloride and bromide.

Advantageously, X is selected from the group of substituted phenyls, where the substituents (Z) can be selected from the group —H, —OH, —F, —Cl, —Br, —I, —OMe, —NH$_2$, —CN, acetyl and can be identical or different.

Particularly advantageously, X is selected from the group of the phenyl groups substituted with one or more hydroxyl groups, where the substituent (Z) can be selected from the group —H, —OH, —F, —Cl, —Br, —I, —OMe, —NH$_2$, —CN, acetyl and the following generic structure is preferred in which Y, $R^1$ and $R^2$ can have the properties defined above.

Of particular advantage are those compounds in which X=

Y=H
$R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cy- cloalkyl-alkylhydroxy, —C₁-C₂₄ alkylhydroxy (linear and branched), —C₁-C₂₄ alkylamine (linear and branched), —C₁-C₂₄-alkylaryl (linear and branched), —C₁-C₂₄-alkylaryl-alkyl-hydroxy (linear and branched), —C₁-C₂₄-alkyl-heteroaryl (linear and branched), —C₁-C₂₄-alkyl-O—C₁-C₂₄-alkyl (linear and branched), —C₁-C₂₄ alky-morpholino, —C₁-C₂₄ alky-piperidino, —C₁-C₂₄ alky-piperazino, —C₁-C₂₄ alky-piperazino-N-alkyl,
R₂=H, —C₁-C₂₄-alkyl (linear and branched),
Z=—H, —OH, —F, —Cl, —Br, —I, —OMe, —NH₂, —CN, acetyl.

Particular preference is given to those compounds in which
X=

Y=H
R₁=—C₁-C₂₄-alkyl (linear and branched), —C₁-C₂₄-alkenyl (linear and branched), —C₁-C₈-cycloalkyl, —C₁-C₈-cycloalkyl-alkylhydroxy, —C₁-C₂₄ alkylhydroxy (linear and branched), —C₁-C₂₄ alkylamine (linear and branched), —C₁-C₂₄-alkylaryl (linear and branched), —C₁-C₂₄-alkylaryl-alkyl-hydroxy (linear and branched), —C₁-C₂₄-alkyl-heteroaryl (linear and branched), —C₁-C₂₄-alkyl-O—C₁-C₂₄-alkyl (linear and branched), —C₁-C₂₄ alky-morpholino, —C₁-C₂₄ alky-piperidino, —C₁-C₂₄ alky-piperazino, —C₁-C₂₄ alky-piperazino-N-alkyl,
R²=H.

The compounds

N-(4-(2,4-dihydroxyphenyl)thiazol-2-yl)heptanamide

N-(4-(2,4-dihydroxyphenyl)thiazol-2-yl)-6-hydroxyhexanamide

N-(4-(2,4-dihydroxyphenyl)thiazol-2-yl)-3-hydroxyhexanamide

N-(4-(2,4-dihydroxyphenyl)thiazol-2-yl)pivalamide

N-(4-(2,4-dihydroxyphenyl)thiazol-2-yl)isobutyramide

N-(4-(2,4-dihydroxyphenyl)thiazol-2-yl)-2-methoxyacetamide

N-(4-(2,4-dihydroxyphenyl)thiazol-2-yl)butyramide

3-amino-N-(4-(2,4-dihydroxyphenyl)thiazol-2-yl)propanamide

N-(4-(2,4-dihydroxyphenyl)thiazol-2-yl)acetamide

N-(4-(2,4-dihydroxyphenyl)thiazol-2-yl)-4-(hydroxymethyl)cyclohexanecarboxamide

N-(4-(2,4-dihydroxyphenyl)thiazol-2-yl)cyclohexanecarboxamide
and

N-(4-(2,4-dihydroxyphenyl)thiazol-2-yl)-2-(4-(hydroxymethyl)phenyl)acetamide
are the preferred ones according to the invention.

The prophylaxis and/or the cosmetic or dermatological treatment with the active ingredient used according to the invention and/or with the cosmetic or topical dermatological preparations with an effective content of active ingredient used according to the invention takes place in the usual manner, and specifically in such a way that the active ingredient used according to the invention and/or the cosmetic or topical dermatological preparations with an active content of active ingredient used according to the invention is applied to the affected areas of skin.

The active ingredient used according to the invention can advantageously be incorporated into customary cosmetic and dermatological preparations, which can be in various forms. Thus, they can be e.g. a solution, an emulsion of the water-in-oil (W/O) type or of the oil-in-water (O/W) type, or a multiple emulsions, for example of the water-in-oil-in-water (W/O/W) type or oil-in-water-in-oil (O/W/O) type, a hydrodispersion or lipodispersion, a Pickering emulsion, a gel, a solid stick or else an aerosol.

Emulsions according to the invention in the context of the present invention, e.g. in the form of a cream, a lotion, a cosmetic milk are advantageous and comprise e.g. fats, oils, waxes and/or other fatty bodies, as well as water and one or more emulsifiers, as are customarily used for such a type of formulation.

It is also possible and advantageous in the context of the present invention to add the active ingredient used according to the invention to aqueous systems or surfactant preparations for cleaning the skin and the hair.

It is naturally known to the person skilled in the art that sophisticated cosmetic compositions are mostly inconceivable without customary auxiliaries and additives. These include, for example, consistency regulators, fillers, perfume, dyes, emulsifiers, additional active ingredients such as vitamins or proteins, light protection agents, stabilizers, insect repellents, alcohol, water, salts, antimicrobial, proteolytic or keratolytic substances etc.

Corresponding requirements apply mutatis mutandis to the formulation of medicinal preparations.

Medicinal topical compositions in the context of the present invention generally comprise one or more medicaments in an effective concentration. For the sake of simplicity, reference is made, for a clear distinction between cosmetic and medicinal application and corresponding products, to the legal provisions of the Federal Republic of Germany (e.g. Cosmetics Ordinance, Food and Drugs Act).

In this connection, it is likewise advantageous to add the active ingredient used according to the invention as additive to preparations which already comprise other active ingredients for different purposes.

Accordingly, cosmetic or topical dermatological compositions can be used in the context of the present invention, depending on their formulation, for example as skin protection cream, cleansing milk, sunscreen lotion, nutrient cream, day or night cream etc. It is likewise possible and advantageous to use the compositions according to the invention as a base for pharmaceutical formulations.

For use, the cosmetic and dermatological preparations are applied, according to the invention, to the skin and/or the hair in an adequate amount in the manner customary for cosmetics.

Particular preference is given to those cosmetic and dermatological preparations which are present in the form of a sunscreen product. These can advantageously additionally comprise at least one further UVA filter and/or at least one further UVB filter and/or at least one inorganic pigment, preferably an inorganic micropigment.

According to the invention, the cosmetic and dermatological preparations can comprise cosmetic auxiliaries, as are customarily used in such preparations, e.g. preservatives, bactericides, perfumes, substances for preventing foaming, dyes, pigments which have a coloring effect, thickeners, moisturizing and/or humectant substances, fats, oil, waxes or other customary constituents of a cosmetic or dermatological formulation, such as alcohols, polyols, polymers, foam stabilizers, electrolytes, organic solvents or silicone derivatives.

An additional content of customary antioxidants is generally preferred. According to the invention, favorable antioxidants that can be used are all antioxidants that are customary or suitable for cosmetic and/or dermatological applications.

The amount of the aforementioned antioxidants (one or more compounds) in the preparations is preferably 0.001 to 30% by weight, particularly preferably 0.05-20% by weight, in particular 1-10% by weight, based on the total weight of the preparation.

If the cosmetic or dermatological preparation in the context of the present invention is a solution or emulsion or dispersion, solvents that can be used are:
water or aqueous solutions
  oils, such as triglycerides of capric acid or caprylic acid, but preferably castor oil;
  fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;
  alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvents, water may be a further constituent.

If the cosmetic or dermatological preparation in the context of the present invention is a solution or emulsion or dispersion, solvents that can be used are:
water or aqueous solutions
  oils, such as triglycerides of capric acid or caprylic acid, but preferably castor oil;
  fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;
  alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvents, water may be a further constituent.

In the context of the present invention, suitable propellants for cosmetic and/or dermatological preparations that can be sprayed from aerosol containers are the customary known, readily volatile, liquefied propellants, for example hydrocarbons (propane, butane, isobutane), which can be used on their own or in a mixture with one another. Compressed air is also to be used advantageously.

The person skilled in the art naturally knows that there are propellant gases that are nontoxic per se which would in principle be suitable for realizing the present invention in the form of aerosol preparations, but which nevertheless have to be dispensed with on account of an unacceptable effect on the environment or other concomitant circumstances, in particular fluorohydrocarbons and chlorofluorohydrocarbons (CFCs).

Cosmetic preparations in the context of the present invention can also be in the form of gels which, besides an effective content of the active ingredient according to the invention and solvents customarily used therefor, preferably water, also comprise organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. aluminum silicates such as, for example, bentonites, or a mixture of polyethylene glycol and polyethylene glycol stearate or distearate. The thickener is present in the gel e.g. in an amount between 0.1 and 30% by weight, preferably between 0.5 and 15% by weight.

It is advantageous according to the invention to use, apart from the combinations according to the invention, further oil-soluble UVA filters and/or UVB filters in the lipid phase and/or further water-soluble UVA filters and/or UVB filters in the aqueous phase.

According to the invention, the light protection formulations can advantageously comprise further substances which absorb UV radiation in the UVB region, where the total amount of the filter substances is e.g. 0.1% by weight to 30% by weight, preferably 0.5 to 10% by weight, in particular 1 to 6% by weight, based on the total weight of the preparations, in order to provide cosmetic preparations which protect the skin from the entire range of ultraviolet radiation. They can also serve as sun protection agents.

BRIEF DESCRIPTION OF THE DRAWINGS

In the attached drawings.

DETAILED DESCRIPTION OF THE INVENTION

Figure 1:
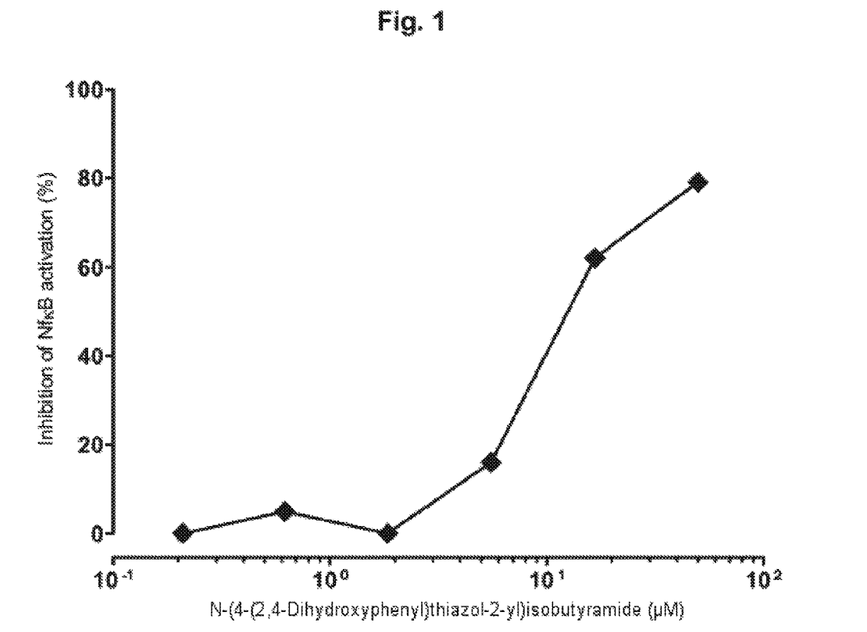
FIG. 1 is a graph showing the inhibition of the inhibition of the activation of NFκB as a function of the concentration of N-(4-(2,4-dihydroxyphenyl)thiazol-2-yl)isobutyramide in the experiment described below.

Demonstration of Effect:

The nuclear factor kappa B (NFκB) is a master regulator of inflammation. The expression of many pro-inflammatory mediators (e.g. cytokines and chemokines) is controlled by NFκB. The inhibition of the activation of NFκB is therefore an important mechanism for minimizing inflammation processes. To measure the NFκB activity, a commercial assay from Cell Culture Service GmbH, Hamburg, was used. In this test, NFκB is activated by adding the pro-inflammatory mediator TNF-alpha. The addition of the alkylamidothiazoles according to the invention prevents the TNF-alpha effect in a dose-dependent manner. FIG. 1 shows the by way of example that even very low concentrations of N-(4-(2,4-dihydroxyphenyl)thiazol-2-yl)isobutyramide prevent the TNF-alpha-induced activation of NFκB.

Figure 2:
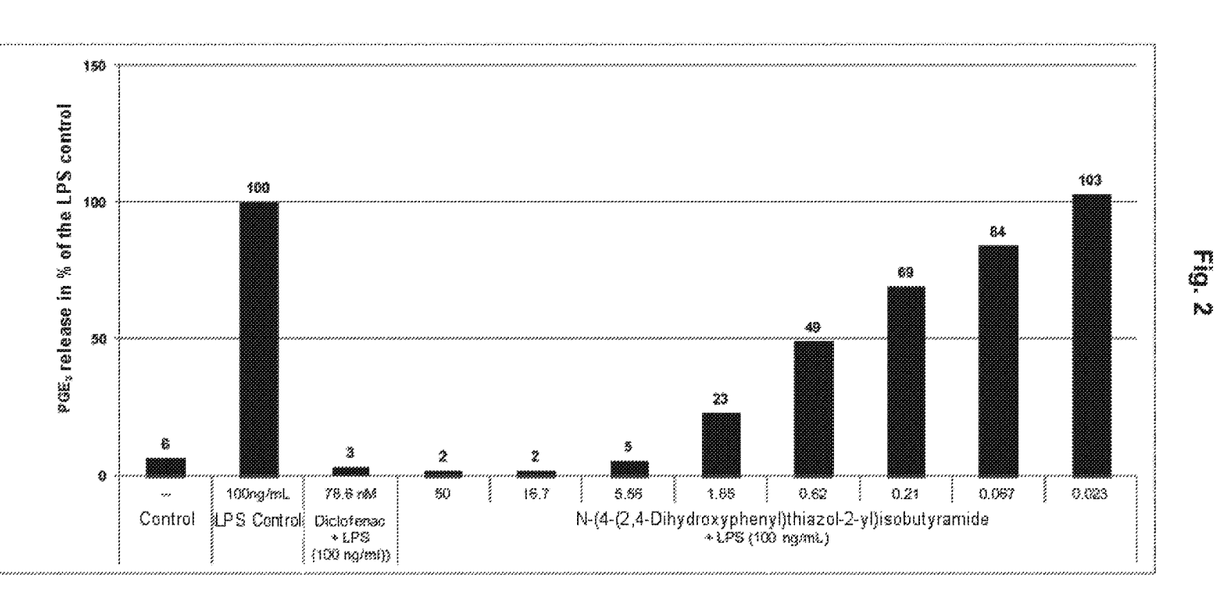
FIG. 2 shows the release of $PGE_2$ at various concentrations of N-(4-(2,4-dihydroxyphenyl)thiazol-2-yl)isobutyramide compared to a control and in the presence of Diclofenac in the experiments described below.
Figure 3:
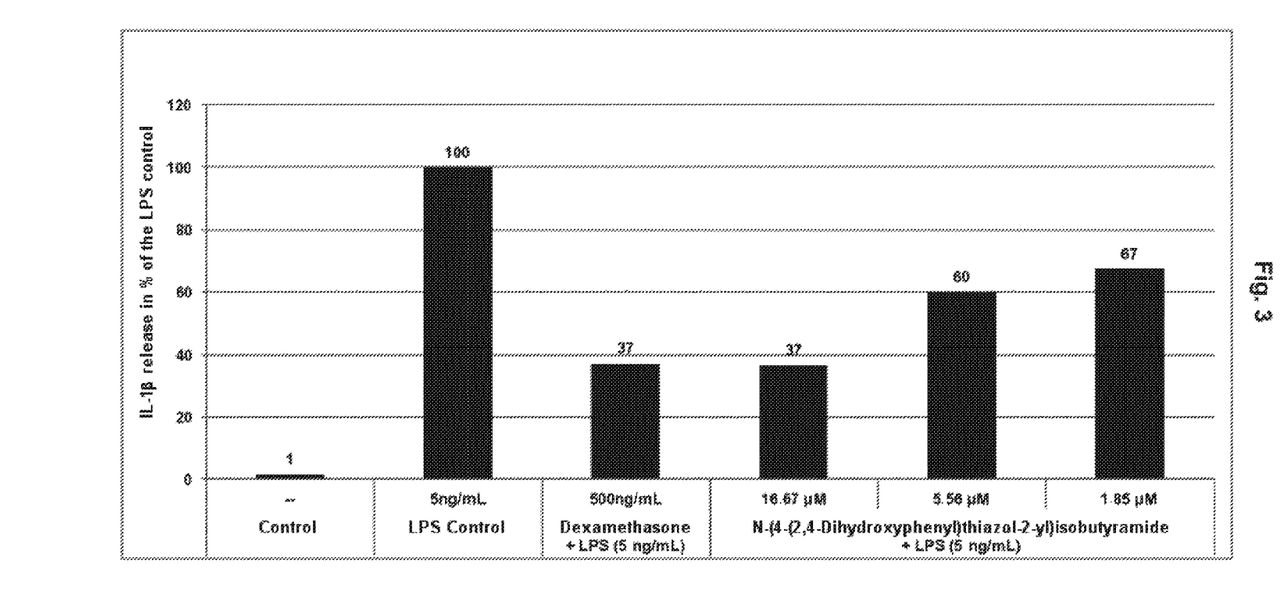
FIG. 3 shows the release of interleukin 1β at various concentrations of N-(4-(2,4-dihydroxyphenyl)thiazol-2-yl)isobutyramide compared to a control and in the presence of Dexamethasone in the experiments described below.

In further experiments it was investigated whether the inhibition of the NFκB activation also actually reduces the subsequent secretion of pro-inflammatory mediators. By way of example, the results of two experiments are documented in the figures. By incubation of human dermal fibroblasts with lipopolysaccharides (LPS), the formation of the pro-inflammatory prostaglandin $E_2$ was induced in the cells, and a specific ELISA was used to determine the concentration in the cell culture supernatant, following incubation for 24 hours with LPS and increasing concentrations of the substances according to the invention. As is evident from FIG. 2, N-(4-(2,4-dihydroxyphenyl)thiazol-2-yl)isobutyramide very significantly reduces the release of $PGE_2$ to a level which is comparable to the pharmacological standard diclofenac. In the next experiment, the release of interleukin 1β (IL-1β) from blood leukocytes following stimulation by LPS and simultaneous incubation (for 24 hours) with the substances according to the invention was measured. Here too, alkylamidothiazoles (here by way of example N-(4-(2,4-dihydroxy-phenyl)thiazol-2-yl)isobutyramide) exhibit a very good anti-inflammatory effectiveness. At a concentration of 16.67 μM, an effectiveness as for 500 ng of dexamethasone, a super-potent corticosteroid, is achieved. The anti-inflammatory activity level of the alkylamidothiazoles is thus that of recognized pharmacological standards, although higher concentrations of the substances according to the invention do have to be used.

Synthesis Procedures of Alkylamidothiazole Selected by Way of Example

2-Bromo-2',4'-bismethoxycarbonyloxyacetophenone

Mitchell, David; Doecke, Christopher W.; Hay, Lynne A.; Koenig Thomas M.; Wirth, David D. Tetrahedron Letters, 1995

A solution of 60 g (369 mmol) of 2,4-dihydroxyacetophenone and 186 ml of triethylamine in 900 ml of tetrahydrofuran was cooled to 0° C., and 93 ml of methyl chloroformate in 400 ml of tetrahydrofuran were slowly added dropwise. A white precipitate is formed. After stirring for 3 hours at room temperature, the reaction is complete (TLC control). The precipitate was filtered off with suction and washed with copious amounts of tetrahydrofuran. The filtrate was evaporated to dryness on a rotary evaporator, taken up in ethyl acetate, washed with 1N HCl and NaCl solution (sat.) and dried over magnesium sulfate, filtered from the magnesium sulfate, and the ethyl acetate was concentrated on a rotary evaporator. 105 g of 2,4-bismethoxycarbonyloxyacetophenone were obtained. $^1$H NMR (DMSO-$D_6$): 8.05 (d, 1H), 7.38 (d, 1H), 7.36 (s, 1H), 3.86 (d, 6H). The product was used without further purification. 63 g (392 mmol) of bromine in 450 ml of chloroform were added dropwise to the solution of 105 g of 2,4-bismethoxycarbo-nyloxyacetophenone in chloroform (1000 ml) over the course of 3 h. The reaction was then stirred for a further 15 min at room temperature The solvent was evaporated on a rotary evaporator. The residue was stirred in ethyl acetate/n-hexane, and the resulting precipitate was filtered off with suction. Recrystallization from ethyl acetate/n-hexane produced 100 g of 2-bromo-2',4'-bismethoxycarbonyloxyacetophenone. $^1$H NMR (DMSO-$D_6$): 8.11 (d, 1H), 7.42 (m, 2H), 4.87 (s, 2H), 3.87 (s, 3H), 3.85 (s, 3H) ppm; m.p. 73-74° C.

N-(4-(2,4-Dihydroxyphenyl)thiazol-2-yl)pivalamide 126 g (1.66 mmol) of thiourea were initially introduced into toluene (1000 ml), and 100 g (829 mmol) of pivaloyl chloride were added. The reaction solution was boiled under reflux for 3 hours, producing two phases. The upper phase was decanted off and cooled. The precipitated colorless needles were filtered off with suction and washed with cyclohexane and dried in vacuo. Yield: 64 g. $^1$H NMR (DMSO-$D_6$): 10.27 (s, 1H), 9.74 (s, 1H), 9.40 (s, 1H), 1.19 (s, 9H) ppm.

107.7 g (310 mmol) of 2-bromo-2',4'-bismethoxycarbonyloxyacetophenone were boiled under reflux for 0.5 h with 49.7 g (13.6 mmol) of N-pivaloylthiourea and 39.2 g (466 mmol) of $NaHCO_3$ in 1.2 l of ethanol. The reaction solution was cooled and admixed with 50.6 g (1.27 mol) of NaOH in 250 ml of water. After stirring for 30 min at room temperature, the reaction solution was taken up with 300 ml of water and neutralized with 2N HCl. The resulting precipitate was filtered off and recrystallized from ethanol/water. 80 g of thiazole were obtained. $^1$H NMR (DMSO-$D_6$): 11.77 (bs, 1H), 11.02 (bs, 1H), 9.47 (bs, 2H), 7.65 (d, 1H), 7.39 (s, 1H), 6.30 (s, 1H), 6.28 (d, 1H), 1.27 (s, 9H) ppm; m.p. 257-259° C.

N-(4-(2,4-Dihydroxyphenyl)thiazol-2-yl)isobutyramide 114 g (1.5 mol) of thiourea were initially introduced into toluene (800 ml), and 80 g (0.75 mol) of isobutyryl chloride were added dropwise. The reaction solution was boiled under reflux for 3 hours, producing two phases. The upper phase was decanted off and cooled. The precipitated white crystals were filtered off with suction and washed with toluene and dried in vacuo. Yield: 62 g. $^1$H NMR (DMSO-$D_6$): 11.03 (bs, 1H), 9.66 (bs, 1H), 9.35 (bs, 1H), 2.72 (m, 1H), 1.03 (2, 6H) ppm;

89 g (260 mmol) of 2-bromo-2',4'-bismethoxycarbonyloxyacetophenone were boiled under reflux for 0.5 h with 37.5 g (260 mmol) of N-isobutyrylthiourea and 32 g (380 mmol) of NaHCO$_3$ in 1000 ml of ethanol. The reaction solution was cooled and admixed with 41 g (0.93 mol) of NaOH in 250 ml of water. After stirring for 30 min at room temperature, the reaction solution was taken up with 300 ml of water and adjusted to pH=3 with 2N HCl. The resulting precipitate was filtered off and recrystallized from ethanol/water. 56 g of thiazole were obtained. $^1$H NMR (DMSO-$D_6$): 12.16 (bs, 1H), 10.88 (bs, 1H), 9.47 (bs, 1H), 7.65 (m, 1H), 7.41 (s, 1H), 6.32 (m, 2H), 2.75 (m, 1H), 1.14 (d, 6H) ppm. m.p.: 243-245° C.

N-(4-(2,4-Dihydroxyphenyl)thiazol-2-yl)butyramide 143 g (1.88 mol) of thiourea were initially introduced into toluene (1000 ml), and 100 g (0.93 mol) of n-butyryl chloride were added dropwise. The reaction solution was boiled under reflux for 3 hours, producing two phases. The upper phase was decanted off and cooled. The precipitated slightly yellowish crystals were filtered off with suction and washed with toluene and dried in vacuo. Yield: 88 g. $^1$H NMR (DMSO-$D_6$): 11.03 (bs, 1H), 9.65 (bs, 1H), 9.33 (bs, 1H), 2.33 (t, 2H), 1.53 (m, 2H), 0.86 (t, 3H) ppm; m.p.: 115-188° C.

92 g (265 mmol) of 2-bromo-2',4'-bismethoxycarbonyloxyacetophenone were boiled under reflux for 0.5 h with 38.75 g (265 mmol) of N-butyrylthiourea and 34 g (397 mmol) of NaHCO$_3$ in 900 ml of ethanol. The reaction solution was cooled and admixed with 37 g (0.93 mol) of NaOH in 300 ml of water. After stirring for 30 min at room temperature, the reaction solution was taken up with 300 ml of water and neutralized with 2N HCl. The resulting precipitate was filtered off and recrystallized from ethanol/water. 67 g of thiazole were obtained. $^1$H NMR (DMSO-$D_6$): 12.18 (bs, 1H), 10.89 (bs, 1H), 9.48 (bs, 1H), 7.65 (1 arom. H), 7.40 (s, 1H), 6.31 (2 arom. H), 2.43 (t, 2H), 1.64 (m, 2H), 0.91 (t, 3H) ppm. m.p.: 227-229° C.

N-(4-(2,4-Dihydroxyphenyl)thiazol-2-yl)acetamide 4.71 g (13.6 mmol) of 2-bromo-2',4'-bismethoxycarbonyloxyacetophenone were boiled under reflux for 0.5 h with 1.61 g (13.6 mmol) of N-acetylthiourea and 1.72 g (20.4 mmol) of NaHCO$_3$ in 45 ml of ethanol. The reaction solution was cooled and admixed with 2.0 g (50 mmol) of NaOH in 20 ml of water. After stirring for 20 min at 0° C., the reaction solution was taken up with 30 ml of water and neutralized with semi-conc. HCl. The resulting precipitate was filtered off and recrystallized from ethanol/water. 2.73 g of product were obtained. ¹H NMR (DMSO-D₆): 12.20 (b, 1H), 10.85 (s, 1H), 9.46 (s, 1H), 7.64 (m, 1H), 7.38 (s, 1H), 6.28 (m, 2H), 2.15 (s, 3H) ppm; m.p. 264-264° C.

N-(4-(2,4-Dihydroxyphenyl)thiazol-2-yl)-4-(hydroxymethyl)cyclohexanecarboxamide Procedure analogous to literature.

BANYU Pharmaceutical Co., Ltd., EP2072519 A1, 2009

Yield: 96%, ¹H NMR (DMSO-D₆): 12.03 (bs, 1H), 3.85, 3.82 (2×d, 2H), 2.50, 2.47 (2×m, 1H), 2.00 (s, 3H), 0.95-1.90 (m, 9H) ppm;

95 g (0.47 mol) of 4-acetoxymethylcyclohexanecarboxylic acid were heated under reflux for 2 h in 350 ml of thionyl chloride. After removing the excess thionyl chloride in vacuo, the residue was taken up in 1 l of toluene, and 71 g (0.94 mol) of thiourea were added. The reaction solution was boiled under reflux for 3 hours and then filtered hot. After cooling the mother liquor, the resulting white crystals were filtered off with suction, washed with toluene and dried in vacuo. Yield: 59 g. ¹H NMR (DMSO-D₆): 11.03, 10.97 (2×s, 1H), 9.64 (bs, 1H), 9.35 (bs, 1H), 3.93, 3.82 (2×d, 2H), 2.61, 2.42 (2×m, 1H), 2.00 (s, 3H), 1.60 (m, 8H), 1.35, 0.94 (2×m, 1H) ppm;

79 g (228 mmol) of 2-bromo-2',4'-bismethoxycarbonyloxyacetophenone were boiled under reflux for 0.5 h with 59 g (228 mmol) of N-(4-acetoxymethylcyclohexylcarbonyl)thiourea and 29 g (340 mmol) of NaHCO₃ in 1000 ml of ethanol. The reaction solution was cooled and admixed with 73 g (1.8 mol) of NaOH in 300 ml of water. After stirring for 30 min at room temperature, the reaction solution was taken up with 300 ml of water and adjusted to pH=3 with 2N HCl. The resulting precipitate was filtered off and recrystallized from ethanol/water. 47 g of thiazole were obtained. ¹H NMR (DMSO-D₆): 12.15, 12.10, (2×s, 1H), 10.96 (2×s, 1H), 9.47 (br, 2H), 7.64 (d, 1H), 7.39 (s, 1H), 6.29 (m, 2H), 4.40 (br, 1H), 3.32, 3.23 (2×d, 2H), 2.65, 2.44 (2×m, 1H), 1.90 (m, 1H), 1.78 (m, 2H), 1.50 (m, 5H), 0.94 (m, 1H) ppm. m.p.: 152-160° C.

N-(4-(2,4-Dihydroxyphenyl)thiazol-2-cyclohexanecarboxamide

52 g (0.68 mol) of thiourea were initially introduced into toluene (500 ml), and 50 g (0.34 mol) of cyclohexanoyl chloride were added dropwise. The reaction solution was boiled under reflux for 3 hours, producing two phases. The upper phase was decanted off and cooled. The precipitated crystals were filtered off with suction, washed with toluene and recrystallized from methanol. Yield: 35 g. $^1$H NMR (DMSO-D$_6$): 10.98 (bs, 1H), 9.65 (bs, 1H), 9.32 (bs, 1H), 2.49 (t, 1H), 1.75 (m, 4H), 1.61 (m, 1H), 1.18 (m, 5H) ppm.

92 g (265 mmol) of 2-bromo-2',4'-bismethoxycarbonyloxyacetophenone were boiled under reflux for 0.5 h with 49.4 g (265 mmol) of N-cyclohexanoylthiourea and 34 g (397 mmol) of NaHCO$_3$ in 900 ml of ethanol. The reaction solution was cooled and admixed with 37 g (930 mmol) of NaOH in 300 ml of water. After stirring for 30 min at room temperature, the reaction solution was taken up with 300 ml of water and neutralized with 2N HCl. The ethanol was largely removed on a rotary evaporator. The resulting precipitate was filtered off and recrystallized from ethanol/water. 70 g of thiazole were obtained. $^1$H NMR (DMSO-D$_6$): 12.14 (bs, 1H), 11.00 (bs, 1H), 9.48 (bs, 1H), 7.64 (1 arom. H), 7.39 (s, 1H), 6.30 (2 arom. H), 2.49 (m, 1H), 1.84 (m, 2H), 1.76 (m, 2H), 1.65 (m, 1H), 1.42 (m, 2H), 1.25 (m, 3H) ppm. m.p.: 262-266° C.

N-(4-(2,4-Dihydroxyphenyl)thiazol-2-yl)-2-(4-(hydroxymethyl)phenyl)acetamide

Procedure analogous to literature.
BANYU Pharmaceutical Co., Ltd., EP2072519 A1, 2009
Yield: 76%, $^1$H NMR (DMSO-D$_6$): 12.31 (bs, 1H), 7.26 (m, 4H), 5.05 (s, 2H), 3.57 (s, 2H), 2.05 (s, 3H) ppm;

3.7 g (18 mmol) of 4-acetoxymethylphenylacetic acid were heated under reflux for 2 h in 40 ml of thionyl chloride. After removing the excess thionyl chloride in vacuo, the residue was taken up in 70 ml of toluene, and 2.7 g (36 mmol) of thiourea were added. The reaction solution was boiled under reflux for 3 hours and then the solvent was removed in vacuo. Purification was carried out by means of column chromatography with cyclohexane/ethyl acetate 1/1 over silica gel. Yield: 2.7 g. $^1$H NMR (DMSO-D$_6$): 11.29 (bs, 1H), 9.55 (bs, 1H), 9.40 (bs, 1H), 7.30 (m, 4H), 5.04 (s, 2H), 3.71 (s, 2H), 2.05 (s, 3H) ppm;

3.5 g (10 mmol) of 2-bromo-2',4'-bismethoxycarbonyloxyacetophenone were boiled under reflux for 0.5 h with 2.7 g (10 mmol) of N-[2-(4-acetoxymethylphenyl)acetyl]thiourea and 1.3 g (15 mmol) of NaHCO$_3$ in 50 ml of ethanol. The reaction solution was cooled and admixed with 4.0 g (0.1 mol) of NaOH in 20 ml of water. After stirring for 2 h at 60° C., the reaction solution was taken up in 100 ml of water and adjusted to pH=3 with 2N HCl. The resulting precipitate was filtered off and recrystallized from ethanol/water. 1.3 g of thiazole were obtained. $^1$H NMR (DMSO-D$_6$): 12.44 (s, 1H), 10.80 (s, 1H), 9.48 (s, 1H), 7.66 (d, 1H), 7.41 (s, 1H), 7.29 (m, 4H), 6.32 (m, 2H), 5.13 (t, 1H), 4.47 (d, 2H), 3.77 (s, 2H) ppm. m.p.: 254-256° C.

The examples below are intended to illustrate the present invention without limiting it. Unless stated otherwise, all quantitative data, fractions and percentages are based on the weight and the total amount or on the total weight of the preparations.

Formulation Examples

O/W Emulsions

| Formulation examples<br>Chemical name | 1<br>% by wt. | 2<br>% by wt. |
|---|---|---|
| PEG-40 stearate | 0.80 | 1.00 |
| Glyceryl stearate | 2.50 | 3.00 |
| C12-15 alkyl benzoate | 2.00 | 2.50 |
| Caprylic/capric triglyceride | 2.00 | 2.50 |
| Cetylstearyl alcohol | 3.00 | 3.00 |

-continued

| Chemical name | | |
|---|---|---|
| Cyclomethicone | 2.00 | 2.00 |
| Dicaprylyl carbonate | — | 2.00 |
| Octyldodecanol | 1.00 | — |
| Triisostearin | — | 0.50 |
| *Butyrospermum parkii* butter | 2.00 | — |
| Octyldodecyl myristate | 1.00 | — |
| Dimethicone | 1.00 | 1.00 |
| Glycerol | 7.50 | 5.00 |
| Methylparaben | 0.20 | — |
| Phenoxyethanol | 0.40 | 0.50 |
| Propylparaben | 0.10 | — |
| Glyceryl caprylate | — | 0.25 |
| Pentylene glycol | — | 0.50 |
| Butylene glycol | 1.00 | — |
| Lauroyl ethyl arginate | 0.10 | 0.05 |
| Potassium sorbate | 0.10 | 0.05 |
| Sodium salicylate | 0.01 | 0.02 |
| Carbomer | 0.15 | 0.10 |
| Sodium polyacrylate | — | 0.20 |
| Xanthan gum | 0.10 | — |
| Acrylates/C10-30 alkyl acrylate crosspolymer | — | 0.10 |
| Trisodium EDTA + water (20% strength aqueous solution) | — | 1.00 |
| Tapioca starch | — | 1.00 |
| Distarch phosphate | — | 1.00 |
| Aluminum starch octenylsuccinate | 2.00 | — |
| Acrylonitrile-methacrylonitrile-methyl methacrylate copolymer + isopentane + magnesium hydroxide | 1.00 | — |
| N-(4-(2,4-Dihydroxyphenyl)thiazol-2-yl)isobutyramide | 0.10 | 0.15 |
| Ethylhexyl methoxycinnaniate | 1.00 | 2.00 |
| Diethylamino hydroxybenzoyl hexyl benzoate | 0.50 | 1.00 |
| Homosalate (3,3,5-trimethyl-cyclohexylsalicylate) | 2.00 | 2.00 |
| Phenylbenzimidazolesulfonic acid | 1.00 | 1.00 |
| Titanium dioxide | — | 1.00 |
| Glyceryl glucoside | 3.00 | — |
| Short-chain hyaluronic acid | — | 0.10 |
| Long-chain hyaluronic acid | 0.10 | — |
| 4-Butylresorcinol | — | 0.10 |
| Magnolia bark extract | 0.10 | — |
| Octadecenedioic acid | — | 0.05 |
| Folic acid | 0.05 | — |
| Carnitine | — | 0.2 |
| Creatine | 0.10 | — |
| Alpha-glucosylrutin | — | 0.01 |
| Taurine | 0.20 | — |
| Mulberry root extract | — | 0.05 |
| Sodium metabisulfite | 0.10 | — |
| Diethylhexyl syringylidenemalonate | 0.13 | 0.13 |
| Sodium hydroxide | q.s. | q.s. |
| 3-Methyl-5-phenyl-1-pentanol | 0.10 | — |
| Coumarin | — | 0.05 |
| Ethyllinalool | 0.01 | — |
| Ascorbyl palmitate | 0.10 | — |
| Perfume | q.s. | q.s. |
| Water | ad 100 | ad 100 |

| | Formulation example | |
|---|---|---|
| | 3 | 4 |
| Chemical name | % by wt. | % by wt. |
| Glyceryl stearate citrate | 2.00 | 1.50 |
| Behenyl alcohol | 1.50 | 1.00 |
| C12-15 alkyl benzoate | 2.00 | 2.50 |
| Caprylic/capric triglyceride | 2.00 | 2.00 |
| Cetyl alcohol | 2.00 | 2.00 |
| Cetylstearyl alcohol | 2.00 | — |
| Cyclopentasiloxane | — | 1.00 |
| Cyclomethicone | 1.00 | 1.00 |
| Dicaprylyl carbonate | — | 2.00 |
| Paraffinum liquidum (mineral oil) | 1.00 | — |
| Octyldodecanol | — | 2.00 |
| Isopropyl palmitate | 1.50 | — |

-continued

| Dimethicone | 0.50 | 1.00 |
|---|---|---|
| Glycerol | 3.00 | 5.00 |
| Methylparaben | 0.20 | 0.15 |
| Phenoxyethanol | 0.40 | 0.60 |
| Propylparaben | 0.10 | — |
| Methylisothiazolinone | — | 0.05 |
| Piroctone olamine | 0.10 | — |
| Sodium benzoate | 0.10 | 0.10 |
| Glyceryl caprylate | — | 0.50 |
| Ethylparaben | 0.10 | — |
| Carbomer | 0.20 | — |
| Sodium polyacrylate | — | 0.40 |
| Xanthan gum | 0.10 | — |
| Acrylates/C10-30 alkyl acrylate crosspolymer | — | 0.10 |
| Tapioca starch | 0.50 | — |
| Nylon-12 (1,8-diazacyclotetradecane-2,7-dione homopolymer) | 1.00 | — |
| Polymethylsilsesquioxane | — | 1.00 |
| Aluminum starch octenylsuccinate | — | 1.00 |
| N-(4-(2,4-Dihydroxyphenyl)thiazol-2-yl)isobutyramide | 0.25 | 0.15 |
| N-(4-(2,4-Dihydroxyphenyl)thiazol-2-yl)pivalamide | 0.10 | 0.10 |
| N-(4-(2,4-Dihydroxyphenyl)thiazol-2-yl)butyramide | 0.01 | 0.25 |
| N-(4-(2,4-Dihydroxyphenyl)thiazol-2-yl)cyclohexanecarboxamide | 0.20 | 0.10 |
| *Glycyrrhiza Inflata* root extract | 0.03 | 0.05 |
| Titanium dioxide | — | 1.00 |
| Octocrylene | 1.00 | 2.00 |
| Bis-ethylhexyloxyphenol methoxyphenyl triazine | 1.00 | 1.00 |
| 2-Ethylhexyl methoxycinnamate | 2.00 | 2.00 |
| Homosalate (3,3,5-trimethylcyclohexyl salicylate) | 1.00 | 1.00 |
| Sodium hydroxide | q.s. | q.s. |
| Trisodium EDTA | 0.15 | — |
| 1-(1,2,3,4,5,6,7,8-octahydro-2,3,8,8,-tetramethyl-2-naphthyl)ethan-1-one | 0.1 | — |
| Geraniol | — | 0.05 |
| Hexylcinnamal | 0.10 | — |
| Perfume | 0.10 | 0.20 |
| Water | ad 100 | ad 100 |

| Formulation examples | 5 | 6 |
|---|---|---|
| Chemical name | % by wt. | % by wt. |
| Polyglyceryl-3 methylglucose distearate | 2.00 | 2.50 |
| Sorbitan stearate | 1.50 | 3.00 |
| C12-15 alkyl benzoate | 2.50 | 2.50 |
| Caprylic/capric triglycerides | 2.50 | 2.50 |
| Stearyl alcohol | 1.00 | 1.50 |
| Cyclomethicone | 3.00 | 1.00 |
| Isopropyl myristate | — | 2.50 |
| Isopropyl palmitate | 2.00 | — |
| Ethylhexyl stearate | — | 1.50 |
| Dimethicone | — | 1.00 |
| Decyl oleate | — | 1.50 |
| Glycerol | 5.00 | 7.50 |
| *Butyrospermum parkii* butter | 2.00 | — |
| Squalane | 0.50 | — |
| Sodium benzoate | 0.10 | 0.10 |
| Methylparaben | 0.20 | 0.20 |
| Phenoxyethanol | 0.40 | 0.40 |
| Propylparaben | 0.10 | — |
| Benzothonium chloride | — | 0.10 |
| Caprylyl glycol | — | 0.20 |
| Ethylhexyl glycerol | — | 0.20 |
| Pentylene glycol | — | 0.10 |
| Carbomer | 0.15 | 0.10 |
| Ammonium acryloyldimethyltaurate/VP copolymer | — | 0.20 |
| Carrageenan | 0.10 | — |
| Trisodium EDTA | — | 1.00 |
| Tapioca starch | — | 1.00 |
| Distarch phosphate | — | 1.00 |
| Acrylonitrile-methacrylonitrile-methyl methacrylate copolymer + isopentane + magnesium hydroxide | 1.00 | — |

-continued

| | | |
|---|---|---|
| N-(4-(2,4-Dihydroxyphenyl)thiazol-2-yl)isobutyramide | 0.01 | 0.25 |
| N-(4-(2,4-Dihydroxyphenyl)thiazol-2-yl)pivalamide | 0.20 | 0.10 |
| N-(4-(2,4-Dihydroxyphenyl)thiazol-2-yl)butyramide | 0.25 | 0.15 |
| N-(4-(2,4-Dihydroxyphenyl)thiazol-2-yl)cyclohexanecarboxamide | 0.10 | 0.10 |
| Diethylamino hydroxybenzoyl hexyl benzoate | 1.00 | 2.00 |
| Ethylhexyl methoxycinnamate | 1.00 | 1.00 |
| Butylmethoxydibenzoylmethane | 2.00 | 2.00 |
| Octocrylene | 1.00 | 1.00 |
| Titanium dioxide | — | 0.50 |
| Sodium hydroxide | q.s. | q.s. |
| Ubiquinone | 0.10 | — |
| Sodium metabisulfite | — | 0.15 |
| BHT (tert-butylhydroxytoluene) | 0.10 | — |
| Linaly acetate | 0.05 | — |
| Hexyl salicylate | — | 0.05 |
| Benzyl salicylate | 0.10 | — |
| Perfume | q.s. | q.s. |
| Water | ad 100 | ad 100 |

What is claimed is:

1. A method for the treatment or prophylaxis of sensitive skin, itching, dry skin, as well as of inflammatory states of the human skin, wherein the method comprises applying to skin of a subject in need thereof a cosmetic or dermatological preparation comprising one or more alkylamidothiazoles of the following formula in an amount which is effective for the treatment or prophylaxis of sensitive skin, itching, dry skin, inflammatory states of the human skin:

in which
R$^1$, R$^2$, X and Y are different, partly identical or completely identical and, independently of one another, represent:
R$^1$=—C$_1$-C$_{24}$-alkyl (linear and branched), —C$_1$-C$_{24}$-alkenyl (linear and branched), —C$_1$-C$_8$-cycloalkyl, —C$_1$-C$_8$-cycloalkyl-alkylhydroxy, —C$_1$-C$_{24}$-alkylhydroxy (linear and branched), —C$_1$-C$_{24}$ alkylamine (linear and branched), —C$_1$-C$_{24}$-alkylaryl (linear and branched), —C$_1$-C$_{24}$-alkylaryl-alkyl-hydroxy (linear and branched), —C$_1$-C$_{24}$-alkylheteroaryl (linear and branched), —C$_1$-C$_{24}$-alkyl-O—C$_1$-C$_{24}$-alkyl (linear and branched), —C$_1$-C$_{24}$ alkyl-morpholino, —C$_1$-C$_4$ alkyl-piperidino, —C$_1$-C$_{24}$ alkyl-piperazino, or —C$_1$-C$_{24}$ alkyl-piperazino-N-alkyl;
R$_2$=H, —C$_1$-C$_{24}$-alkyl (linear and branched), —C$_1$-C$_{24}$-alkenyl (linear and branched), —C$_1$-C$_8$-cycloalkyl, —C$_1$-C$_{24}$-hydroxyalkyl (linear and branched), —C$_1$-C$_{24}$-alkylaryl (linear and branched), or —C$_1$-C$_{24}$-alkylheteroaryl (linear and branched);
X=-phenyl, optionally mono- or polysubstituted with —OH, —F, —Cl, —Br, —I, —OMe, —NH$_2$, —CN, or cetyl;
Y=H, —C$_1$-C$_{24}$-alkyl (linear and branched), —C$_1$-C$_{24}$-alkenyl (linear and branched), —C$_1$-C$_8$-cycloalkyl, —C$_1$-C$_{24}$-aryl, —C$_1$-C$_{24}$-heteroaryl, —C$_1$-C$_{24}$-alkylaryl (linear and branched), —C$_1$-C$_{24}$-alkylheteroaryl (linear and branched), -phenyl, -2,4-dihydroxyphenyl, -2,3-dihydroxyphenyl, -2,4-dimethoxyphenyl, -2,3-dimethoxyphenyl, —COO-alkyl, —COO— alkenyl, —COO-cycloalkyl, —COO-aryl, or —COO-heteroaryl;
and wherein the one or more alkylamidothiazoles are present as a free base and/or as a cosmetically and dermatologically acceptable salt thereof.

2. The method of claim 1, wherein X represents phenyl mono- or polysubstituted with —OH, —F, —Cl, —Br, —I, —OMe, —NH$_2$, —CN, or acetyl.

3. The method of claim 2, wherein the one or more alkylamidothiazoles comprise one or more alkylamidothiazoles of formula where the substituents Z independently represent —H, —OH, —F, —Cl, —Br, —I, —OMe, —NH$_2$, —CN, or acetyl.

4. The method of claim 3, wherein the one or more alkylamidothiazoles comprise one or more alkylamidothiazoles of formula where Z represents —H, —OH, —F, —Cl, —Br, —I, —OMe, —NH$_2$, —CN, or acetyl.

5. The method of claim 1, wherein the preparation comprises one or more alkylamidothiazoles of formula in which

X=

Y=H;

R¹=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$ alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alkyl-morpholino, —$C_1$-$C_{24}$ alkyl-piperidino, —$C_1$-$C_{24}$ alkyl-piperazino, or —$C_1$-$C_{24}$ alky-piperazino-N-alkyl;

$R_2$=H, or —$C_1$-$C_{24}$-alkyl (linear and branched);

and Z=—H, —OH, —F, —Cl, —Br, —I, —OMe, —$NH_2$, —CN, or acetyl.

6. The method of claim 1, wherein the preparation comprises one or more alkylamidothiazoles of formula in which

X=

Y=H;

R¹=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$ alkylamine (linear and branched), —$C_1$-$C_{24}$-alkylaryl (linear and branched), —$C_1$-$C_{24}$-alkyl-aryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alkyl-morpholino, —$C_1$-$C_{24}$ alkyl-piperidino, —$C_1$-$C_{24}$ alkyl-piperazino, or —$C_1$-$C_{24}$ alkyl-piperazino-N-alkyl;

and $R_2$=H.

7. The method of claim 1, wherein the preparation comprises one or more of the following alkylamidothiazoles:

N-(4-(2,4-dihydroxyphenyl)thiazol-2-yl)pivalamide

N-(4-(2,4-dihydroxyphenyl)thiazol-2-yl)isobutyramide

N-(4-(2,4-dihydroxyphenyl)thiazol-2-yl)butyramide

N-(4-(2,4-dihydroxyphenyl)thiazol-2-yl)heptanamide

N-(4-(2,4-dihydroxyphenyl)thiazol-2-yl)-6-hydroxyhexanamide

N-(4-(2,4-dihydroxyphenyl)thiazol-2-yl)-3-hydroxypropanamide

N-(4-(2,4-dihydroxyphenyl)thiazol-2-yl)-2-methoxyacetamide

3-amino-N-(4-(2,4-dihydroxyphenyl)thiazol-2-yl)-2-propanamide

N-(4-(2,4-dihydroxyphenyl)thiazol-2-yl)acetamide

N-(4-(2,4-dihydroxyphenyl)thiazol-2-yl)-4-(hydroxymethyl)cyclohexanecarboxamide

N-(4-(2,4-dihydroxyphenyl)thiazol-2-yl)cyclohexanecarboxamide and

N-(4-(2,4-dihydroxyphenyl)thiazol-2-yl)-2-(4-(hydroxymethyl)phenyl)acetamide.

8. The method of claim 1, wherein the preparation comprises

N-(4-(2,4-dihydroxyphenyl)thiazol-2-yl)isobutyramide.

9. The method of claim 1, wherein the preparation comprises one or more alkylamidothiazoles in the form of one or more of a halide, a carbonate, an ascorbate, a sulfate, an acetate, or a phosphate.

10. The method of claim 1, wherein the preparation comprises from 0.000001 to 10.0% by weight of the one or more alkylamidothiazoles, based on a total weight of the preparation.

11. The method of claim 10, wherein the preparation comprises from 0.0001 to 3.0% by weight of the one or more alkylamidothiazoles.

12. The method of claim 10, wherein the preparation comprises from 0.001 to 1% by weight of the one or more alkylamidothiazoles.

13. The method of claim 7, wherein the preparation comprises from 0.0001 to 3.0% by weight of the one or more alkylamidothiazoles, based on a total weight of the preparation.

14. The method of claim 13, wherein the preparation comprises from 0.001 to 1% by weight of the one or more alkylamidothiazoles, based on a total weight of the preparation.

15. The method of claim 1, wherein itching is treated.

16. The method of claim 1, wherein sensitive skin is treated.

17. The method of claim 1, wherein dry skin is treated.

18. The method of claim 1, wherein inflammatory states in the human skin are treated.

19. The method of claim 1, wherein sensitive skin is prevented.

20. The method of claim 1, wherein dry skin is prevented.

* * * * *